US011773352B2

(12) United States Patent
Smith et al.

(10) Patent No.: US 11,773,352 B2
(45) Date of Patent: Oct. 3, 2023

(54) HYDROCHLOROFLUOROOLEFINS AND METHODS OF USING SAME

(71) Applicant: 3M INNOVATIVE PROPERTIES COMPANY, St. Paul, MN (US)

(72) Inventors: Sean M. Smith, Woodbury, MN (US); Michael J. Bulinski, Stillwater, MN (US); Michael G. Costello, Afton, MN (US); Forrest A. Coughlin, Chaska, MN (US); Hui Ren, Woodbury, MN (US); Zai-Ming Qiu, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 285 days.

(21) Appl. No.: 17/416,830

(22) PCT Filed: Dec. 20, 2019

(86) PCT No.: PCT/IB2019/061226
§ 371 (c)(1),
(2) Date: Jun. 21, 2021

(87) PCT Pub. No.: WO2020/136533
PCT Pub. Date: Jul. 2, 2020

(65) Prior Publication Data
US 2022/0056382 A1    Feb. 24, 2022

Related U.S. Application Data

(60) Provisional application No. 62/784,890, filed on Dec. 26, 2018.

(51) Int. Cl.
| | | |
|---|---|---|
| *C09K 5/04* | (2006.01) | |
| *C11D 7/50* | (2006.01) | |
| *C07C 43/17* | (2006.01) | |
| *C07C 43/172* | (2006.01) | |
| *C11D 7/28* | (2006.01) | |
| *C11D 11/00* | (2006.01) | |

(52) U.S. Cl.
CPC ............ *C11D 7/5018* (2013.01); *C07C 43/17* (2013.01); *C07C 43/172* (2013.01); *C11D 7/28* (2013.01); *C11D 11/0047* (2013.01)

(58) Field of Classification Search
CPC .................................................... C09K 5/045
USPC ........................................................ 252/67
See application file for complete search history.

(56) References Cited

U.S. PATENT DOCUMENTS

| | | | |
|---|---|---|---|
| 2,613,228 A | 10/1952 | Ruh | |
| 3,551,395 A | 12/1970 | Schaum | |
| 5,087,775 A | 2/1992 | Gassen | |
| 5,114,515 A | 5/1992 | Birdwell | |
| 6,734,154 B2 | 5/2004 | Flynn | |
| 8,486,295 B2 * | 7/2013 | Bartelt | C09K 5/10 252/67 |
| 8,642,819 B2 | 2/2014 | Elsheikh | |
| 2011/0041529 A1 | 2/2011 | Chen | |
| 2016/0145195 A1 | 5/2016 | Bulinski | |
| 2017/0369668 A1 | 12/2017 | Chen | |

FOREIGN PATENT DOCUMENTS

WO    WO 2009-079525    6/2009

OTHER PUBLICATIONS

Alam, "Measurement of thermal conductivity and correlations at saturated state of refrigerant trans-1-chloro-3,3,3-trifluoropropene (R-1233zd(E))", International Journal of Refrigeration, Jun. 2018, vol. 90, pp. 174-180.

Ellis, Cleaning and Contamination of Electronics Components and Assemblies, 182-194 (1986).

Henne, "Behaviour of Fluorinated Olefines Towards Anionic Reagents", Journal of Indian Chemical Society, Jul. 1953, vol. 30, No. 12, pp. 809-814.

Krespan, "Negative Substituents in the Claisen rearrangement", Tetrahedron 1967, vol. 23, pp. 4243-4249.

Ono, "Liquid-phase photofluorination with elemental fluorine. Part III. Synthesis of perfluorocycloalkyl ethers with/without a chlorine substituent", Journal of Fluorine Chemistry, 1995, vol. 75, pp. 197-204.

Park, "Action of Alcohols on 3,3,4,4-Tetrafluoro-1,2-dichlorocyclobutene-$1^{1,2}$", Journal of the American Chemistry Society, May 1951, vol. 73, pp. 2342-2345.

Park, "The Reactions of Some Alicyclic 1,2-Dihalopolyfluoro Olefins with Ethanolic Potassium Hydroxide. The Effect of Ring Size on Product Distribution", The Journal of Organic Chemistry, Jan. 1968, vol. 33, No. 1, pp. 33-37.

PubChem CID 129812029, Sep. 13, 2017, Retrieved from the Internet <URL https//pubchemncbinlm nih gov/compound/ 129812029>, 7 pages.

International Search Report for PCT International Application No. PCT/IB19/61226, dated Apr. 14, 2020, 2 pages.

* cited by examiner

*Primary Examiner* — Gregory E Webb

(74) *Attorney, Agent, or Firm* — Jeffrey M. Olofson

(57) ABSTRACT

A composition including a compound having structural formula (I): $R_f$ is a linear or branched perfluoroalkyl group having 1-3 atoms; n is 0-2; x is 1-3; and $R_{f'}$ and $R_{f''}$ are (i) independently, a linear or branched perfluoroalkyl group having 1-8 carbon atoms; or (ii) are bonded together to form a ring structure having 4-8 carbon atoms. The composition further includes a hydrocarbon contaminant.

12 Claims, No Drawings

HYDROCHLOROFLUOROOLEFINS AND METHODS OF USING SAME

FIELD

The present disclosure relates to hydrochlorofluoroolefins and methods of making and using the same, and to working fluids that include the same.

BACKGROUND

Various olefinic compounds are described in, for example, A. L. Henne et al., *Jour. Indian Chem.* 1953, 80, 809-814; Md. J. Alam et al., *International Journal of Refrigeration* 2018, 90, 174-180; U.S. Pat. App. Pub. 2017/0369668; and U.S. Pat. No. 8,642,819.

SUMMARY

In some embodiments, a composition is provided. The composition incudes a compound having structural formula (I):

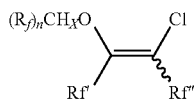

where $R_f$ is a linear or branched perfluoroalkyl group having 1-3 atoms; n is 0-2; x is 1-3; and $R_f'$ and $R_f''$ are (i) independently, a linear or branched perfluoroalkyl group having 1-8 carbon atoms; or (ii) are bonded together to form a ring structure having 4-8 carbon atoms; with the provisos that: when n is 0, then x is 3; when n is 1 then x is 2; and when n is 2 then x is 1. The composition further includes a hydrocarbon contaminant.

In some embodiments, a process for removing contaminants from a substrate is provided. The process includes contacting a substrate with a compound having structural formula (I):

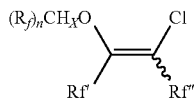

where $R_f$ is a linear or branched perfluoroalkyl group having 1-3 atoms; n is 0-2; x is 1-3; and $R_f'$ and $R_f''$ are (i) independently, a linear or branched perfluoroalkyl group having 1-8 carbon atoms; or (ii) are bonded together to form a ring structure having 4-8 carbon atoms; with the provisos that: when n is 0, then x is 3; when n is 1 then x is 2; and when n is 2 then x is 1. The contaminant comprises a hydrocarbon.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

The ever-increasing demand for reliability, continuing miniaturization, and the growing number of faults in electronic components manufactured in no-clean processes all combine to put increased focus on the use of cleaning solvents in electronics manufacturing. There has been rapid growth in the electronics industry on account of the swiftly rising demand for industrial as well as consumer electronics products. Cleaning solvents are specially engineered to dependably dissolve common manufacturing greases and oils (e.g., hydrocarbons having the formula $C_nH_{2n+2}$, where n is 5-25) used in the production of such industrial and consumer electronics products. Fluorinated cleaning solvents which demonstrate high levels of hydrocarbon solubility are suitable for such applications, in part, due to their low flammability, high density, low viscosity, low surface tension, and higher vapor pressure resulting in quick evaporation from components after use. Furthermore, in sharp contrast to hydrocarbon solvents, fluorinated cleaning solvents minimize the amount of residue left on components after cleaning.

Currently, fluids used for dissolving and removing such greases and oils (i.e., long chain hydrocarbons), or other organics from surfaces contain fluid blends that include, for example, trans-di-chloro-ethylene, 1,1,1-trichloroethane (TCA), trichloroethylene, and dichloromethane. Regarding such fluid blends, one drawback to this approach is the tendency for a change in the composition ratio over the lifetime of the cleaning fluid. This change in composition ratio, in turn, leads to safety concerns and also compromises the performance of the cleaning fluid. Therefore, a single composition cleaning fluid which is nontoxic, nonflammable, and high in hydrocarbon solubility would be of significant benefit to the electronics cleaning industry. Moreover, some of the materials currently employed are regulated by the Montreal Protocol as ozone depleting substances or have toxicity concerns.

In view of an increasing demand for environmentally friendly and low toxicity chemical compounds, in addition to strong cleaning ability, there exists a need for new long chain hydrocarbon alkanes cleaning fluids that provide low environmental impact and toxicity. Finally, such cleaning fluids should be capable of being manufactured using cost-effective methods.

Generally, the present disclosure provides a new class of compounds useful as cleaning fluids (or as components of cleaning fluids). The compounds are hydrochlorofluoroolefin ethers, which provide better cleaning and physical properties to existing cleaning fluids, as well as provide lower atmospheric lifetimes and lower global warming potentials to provide a more acceptable environmental profile. Furthermore, the hydrochlorofluoroolefin ethers of the present disclosure can be manufactured cost-effectively.

As used herein, "halogenated" (for example, in reference to a compound or molecule, such as in the case of "halogenated HFO") means that there is at least one carbon-bonded halogen atom.

As used herein, "fluoro-" (for example, in reference to a group or moiety, such as in the case of "fluoroalkylene" or "fluoroalkyl" or "fluorocarbon") or "fluorinated" means (i) partially fluorinated such that there is at least one carbon-bonded hydrogen atom, or (ii) perfluorinated.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to a compound having structural formula (I):

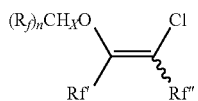

I where $R_f$ is a linear or branched perfluoroalkyl group having 1-3 or 1-2 carbon atoms; n is 0-2 or 1-2; x is 1-3 or 1-2; and $R_f'$ and $R_f''$ are (i) independently, a linear or branched perfluoroalkyl group having 1-8 carbon atoms, 1-4 carbon atoms, or 1-3 carbon atoms; or (ii) are bonded together to form a ring structure having 4-8 carbon atoms, 5-6 carbon atoms, or 5 carbon atoms; with the proviso that when n is 0 then x is 3; when n is 1 then x is 2; and when n is 2 then x is 1.

It is to be recognized that the compounds of structural formula (I) of the present disclosure (including any structural formulas appearing in the claims), despite what may be depicted in the structural formula, may include the cis isomer, the trans isomer, or a mixture of the cis and trans isomers.

In some embodiments, the compounds of structural formula (I) may possess excellent hydrocarbon solubility, rendering them highly suitable for use as cleaning solvents. In this regard, in some embodiments, any of the above described hydrofluoroolefins may have a solubility factor defined as follows:

Solubility Factor (SF)=((LSH/14)−1)−3.5 ((T−70)/70)$^2$+0.643, where LSH is determined in accordance with the Largest Soluble Hydrocarbon Test of the Examples of the present disclosure and T is the normal boiling point of the fluid (in degrees Celsius). In some embodiments, LSH (at room temperature) may vary from 14 to 25 17 to 23, or 17 to 21, in whole number increments. In some embodiments, any of the above described compounds may have a solubility factor (SF) of greater than 0, greater than 0.1, greater than 0.2, greater than 0.5, greater than 1.0, greater than 1.1, or greater than 1.2.

In various embodiments, representative examples of the compounds of structural formula (I) include the following:

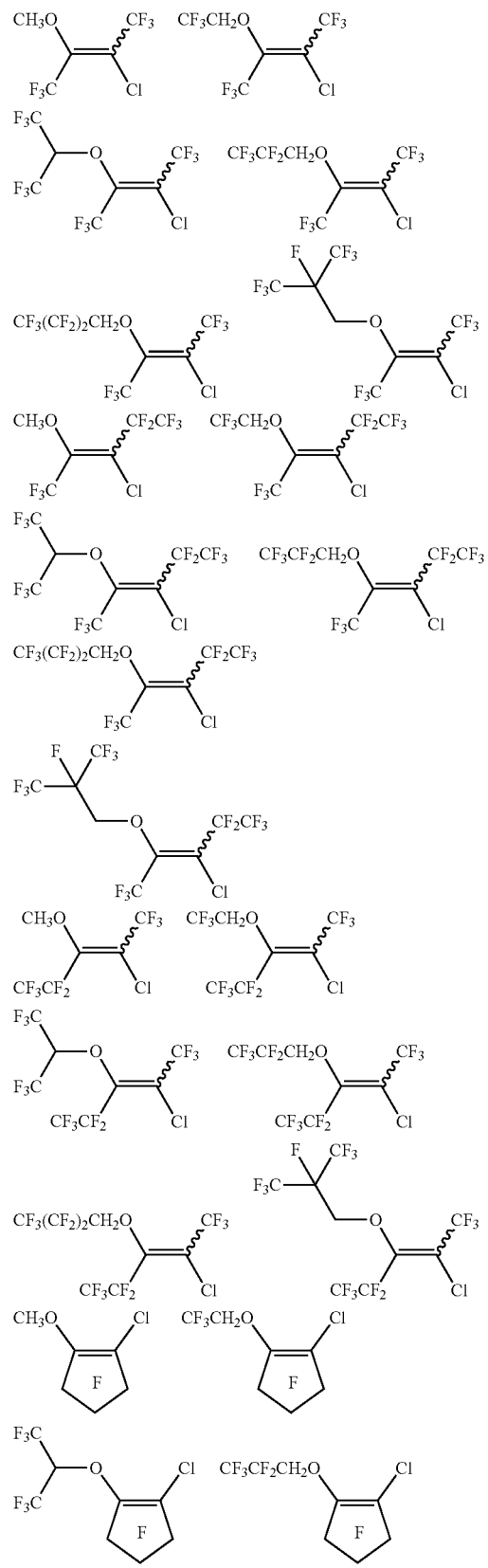

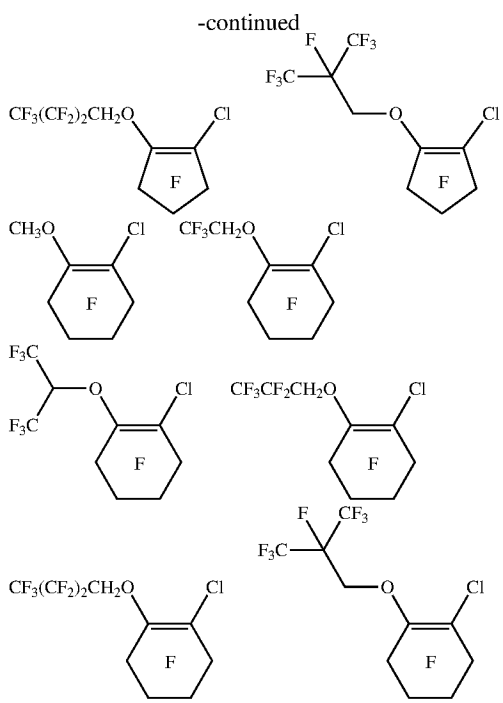

In some embodiments, the compounds of structural formula (I) may be useful over a broad operating temperature range. In this regard, in some embodiments, the compounds may have a boiling point of no lower than 30, 40 or 50 degrees Celsius and no higher than 150, 140, 130, 120, 110, 100, 90, or 80 degrees Celsius.

In some embodiments, the compounds of structural formula (I) may be hydrophobic, relatively chemically unreactive, and thermally stable. The compounds may have a low environmental impact. In this regard, the compounds of the present disclosure may have a global warming potential (GWP) of less than 200, 150, 100, 50 or less than 10. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation a, is the radiative forcing per unit mass increase of a compound in the atmosphere (the change in the flux of radiation through the atmosphere due to the IR absorbance of that compound), C is the atmospheric concentration of a compound, ti is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the compounds of structural formula (I) may include a fluorine content sufficient to make them non-flammable according to ASTM D-3278-96 e-1 test method ("Flash Point of Liquids by Small Scale Closed Cup Apparatus").

In some embodiments, the compounds of structural formula (I) may have surprisingly low acute toxicity. Specifically, in some embodiments, 4-hour acute inhalation toxicity studies in rats demonstrate LC-50 values as high as 5,000 ppm, 10,000 ppm, 15,000 ppm, or 20,000 ppm.

In some embodiments, the compounds of structural formula (I) can be prepared from their respective perfluorinated dichloroolefins (structural formula (II)) in combination with a base (e.g., KOH) and a fluorinated or nonfluorinated alcohol at room temperature (Scheme 1). Related literature has described their preparation. See *J. of Indian Chemical Society* 1953, 30, 809-814 and references cited therein.

Scheme 1

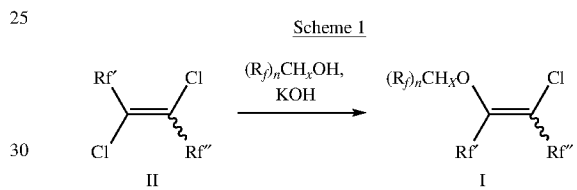

Representative examples of the perfluorinated dichloroolefins include:

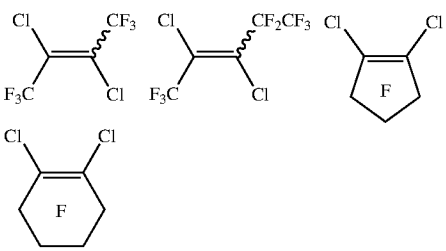

Representative examples of fluorinated and nonfluorinated alcohols include:

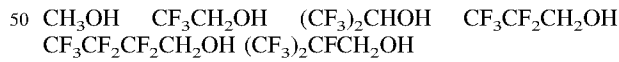

In some embodiments, the present disclosure is further directed to working fluids that include the compounds of structural formula (I) as a major component. For example, the working fluids may include at least 25%, at least 50%, at least 70%, at least 80%, at least 90%, at least 95%, or at least 99% by weight of the compounds of structural formula (I), based on the total weight of the working fluid. In addition to the compounds of structural formula (I), the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrochloroolefins, hydrochlorofluoroolefins, hydrofluoroethers, or mixtures thereof, based on the total weight of the working fluid. Such additional components can be chosen to modify or enhance the properties of a composition for a particular use.

In some embodiments, the present disclosure relates to cleaning compositions that include one or more compounds of structural formula (I). In use, the cleaning compositions may serve to remove (e.g., dissolve) contaminants from the surface of a substrate. In this regard, the present disclosure is further directed to compositions that include one or more compounds of structural formula (I) and one or more contaminants (which have, for example, been removed from a substrate).

In some embodiments, the cleaning compositions of the present disclosure may include one or more co-solvents. Suitable co-solvents may include alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof. Representative examples of co-solvents which can be used in the cleaning compositions may include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene [remove from list?]-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof. For example, such co-solvents can be chosen to modify or enhance the solvency properties of a cleaning composition for a particular use and can be utilized in ratios (of co-solvent to hydrofluoroolefin compounds) such that the resulting composition has no flash point.

In various embodiments, the cleaning compositions may include one or more surfactants. Suitable surfactants include those surfactants that are sufficiently soluble in the compounds of structural formula (I), and which promote contaminant removal by dissolving, dispersing, or displacing the contaminant. One useful class of surfactants are those nonionic surfactants that have a hydrophilic-lipophilic balance (HLB) value of less than about 14. Examples include ethoxylated alcohols, ethoxylatedalkyl phenols, ethoxylated fatty acids, alkylarysulfonates, glycerol esters, ethoxylated fluoroalcohols, and fluorinated sulfonamides. Mixtures of surfactants having complementary properties may be used in which one surfactant is added to the cleaning composition to promote oily contaminant removal and another added to promote water-soluble contaminant removal. The surfactant, if used, can be added in an amount sufficient to promote contaminant removal. Typically, surfactant is added in amounts from 0.1 to 5.0 wt. %, or amounts from about 0.2 to 2.0 wt. %, based on the total weight of the surfactant(s) and the compounds of structural formula (I).

In some embodiments, if desirable for a particular application, the cleaning compositions can further include one or more dissolved or dispersed gaseous, liquid, or solid additives (for example, carbon dioxide gas, stabilizers, antioxidants, or activated carbon).

In some embodiments, the present disclosure is directed to the above-described cleaning compositions, in their post-clean state. In this regard, the present disclosure is directed to any of the above-described cleaning compositions that include one or more contaminants dissolved, dispersed, or otherwise contained therein.

In some embodiments, the contaminants may include light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; water; and other contaminants encountered in precision, electronic, metal, and medical device cleaning can be removed. In some embodiments, the hydrofluoroolefin compounds of the present disclosure may be particularly suited to remove long chain hydrocarbon alkane contaminants (e.g., hydrocarbons having the formula $C_nH_{2n+2}$, where n is greater than 5).

In some embodiments, the contaminants may be present in the post-clean cleaning composition (individually or collectively) in an amount of between 0.0001% and 20 wt. %, between 0.001 and 10 wt. %, or between 0.01 and 5 wt. %; or at least 0.0001 wt. %, at least 0.001 wt. %, or at least 0.01 wt. %, based on the total weight of the compounds of structural formula (I) in the post-clean composition.

In some embodiments, the present disclosure relates to a process for cleaning a substrate. The cleaning process can be carried out by contacting a contaminated substrate with a cleaning composition as discussed above.

In some embodiments, the cleaning compositions of the present disclosure can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies,* Electrochemical Publications Limited, Ayr, Scotland, pages 182-94 (1986), which is herein incorporated by reference in its entirety.

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices

Listing of Embodiments

1. A composition comprising:

a compound having structural formula (I):

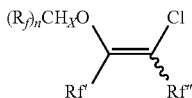

where $R_f$ is a linear or branched perfluoroalkyl group having 1-3 atoms; n is 0-2; x is 1-3; and $R_f'$ and $R_f''$ are (i) independently, a linear or branched perfluoroalkyl group having 1-8 carbon atoms; or (ii) are bonded together to form a ring structure having 4-8 carbon atoms;

with the provisos that:

when n is 0, then x is 3;

when n is 1 then x is 2; and when n is 2 then x is 1; and a hydrocarbon contaminant.

2. The composition of embodiment 1, wherein the hydrocarbon contaminant comprises a hydrocarbon having the formula $C_nH_{2n+2}$, where n is greater than 5.

3. The composition of any one of the previous embodiments, wherein the compound having structural formula (I) is present in the composition at an amount of at least 25% by weight based on the total weight of the composition.

4. The composition of any one of the previous embodiments, wherein the compound having structural formula (I) is present in the composition at an amount of at least 50% by weight based on the total weight of the composition.

5. The composition of any one of the previous embodiments, wherein the hydrocarbon contaminant is present in the composition at an amount of between 0.0001% and 20% by weight, based on the total weight of the compounds of structural formula (I) in the post-clean composition.

6. The composition of any one of the previous embodiments, wherein the composition further comprises a co-solvent.

7. The composition of embodiment 6, wherein said co-solvent comprises alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof.

8. The composition of any one of the previous embodiments, wherein the composition further comprises a surfactant.

9. The composition of embodiment 8, wherein the composition comprises from 0.1 to 5 percent by weight of the surfactant, based on the total weights of the compound having structural formula (I) and the surfactant.

10. The composition according to any one of embodiments 8-9, wherein the surfactant comprises a nonionic surfactant comprising an ethoxylated alcohol, an ethoxylated alkylphenol, an ethoxylated fatty acid, an alkylaryl sulfonate, a glycerolester, an ethoxylated fluoroalcohol, a fluorinated sulfonamide, or mixtures thereof.

11. A process for removing contaminants from a substrate, the process comprising the steps of:

contacting a substrate with a compound having structural formula (I):

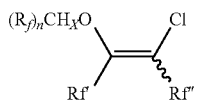

where $R_f$ is a linear or branched perfluoroalkyl group having 1-3 atoms; n is 0-2; x is 1-3; and $R_f'$ and $R_f''$ are (i) independently, a linear or branched perfluoroalkyl group having 1-8 carbon atoms; or (ii) are bonded together to form a ring structure having 4-8 carbon atoms;

with the provisos that when n is 0, then x is 3;

when n is 1 then x is 2; and when n is 2 then x is 1; and wherein the contaminant comprises a hydrocarbon.

12. The process of embodiment 11, wherein the hydrocarbon contaminant comprises a hydrocarbon having the formula $C_nH_{2n+2}$, where n is greater than 5.

EXAMPLES

The operation of the present disclosure will be further described with regard to the following detailed examples. These examples are offered to further illustrate various embodiments and techniques. It should be understood, however, that many variations and modifications may be made while remaining within the scope of the present disclosure.

Unless otherwise noted, all parts, percentages, ratios, etc. in the examples and the rest of the specification are by weight, and all reagents used in the examples were obtained, or are available, from general chemical suppliers such as, for example, Sigma-Aldrich Corp., Saint Louis, Mo., US or may be synthesized by conventional methods.

The following abbreviations are used herein: mL=milliliters, L=liters, mol=moles, mmol=millimoles, W=Watts, min=minutes, hr=hours, g=grams, mmHg=millimeters of mercury, ° C.=degrees Celsius, mp=melting point. "Room temperature" refers to an ambient temperature of approximately 20-25° C., with an average of 23° C.

TABLE 1

Materials

| Material | Description | Source |
| --- | --- | --- |
| MeOH | Methanol | Sigma-Aldrich Corp., Saint Louis, MO, US |
| KOH | Potassium hydroxide | Alfa Aesar, Haverhill, MA, US |
| $CF_3CH_2OH$ | 2,2,2-Trifluoroethanol | Sigma-Aldrich Corp., Saint Louis, MO, US |
| $(CF_3)_2CHOH$ | 1,1,1,3,3,3-hexafluoropropan-2-ol | Oakwood Products, Inc., Augusta, GA, US |
| $CH_3CN$ | Acetonitrile | Sigma-Aldrich Corp., Saint Louis, MO, US |
| $K_2CO_3$ | Potassium carbonate | Alfa Aesar, Haverhill, MA, US |

TABLE 1-continued

Materials

| Material | Description | Source |
|---|---|---|
| Perfluoro-1,2-dichlorocyclopentene | 1,2-Dichloro-3,3,4,4,5,5-hexafluorocyclopent-1-ene | SynQuest Laboratories, Alachua FL, US |
| Perfluoro-2,3-dichlorobut-2-ene | 2,3-Dichloro-1,1,1,4,4,4-hexafluorobut-2-ene | SynQuest Laboratories, Alachua FL, US |
| C-9 hydrocarbon | $C_9H_{20}$, mp = −53.5° C. | Sigma-Aldrich Corp., Saint Louis, MO, US |
| C-10 hydrocarbon | $C_{10}H_{22}$, mp = −29.7° C. | Sigma-Aldrich Corp., Saint Louis, MO, US |
| C-11 hydrocarbon | $C_{11}H_{24}$, mp = −25° C. | Sigma-Aldrich Corp., Saint Louis, MO, US |
| C-12 hydrocarbon | $C_{12}H_{26}$, mp = −9.6° C. | Sigma-Aldrich Corp., Saint Louis, MO, US |
| C-13 hydrocarbon | $C_{13}H_{28}$, mp = −5.4° C. | Sigma-Aldrich Corp., Saint Louis, MO, US |
| C-14 hydrocarbon | $C_{14}H_{30}$, mp = 5.9° C. | Sigma-Aldrich Corp., Saint Louis, MO, US |
| C-15 hydrocarbon | $C_{15}H_{32}$, mp = 9.9° C. | Sigma-Aldrich Corp., Saint Louis, MO, US |
| C-16 hydrocarbon | $C_{16}H_{34}$, mp = 18.2° C. | Sigma-Aldrich Corp., Saint Louis, MO, US |
| C-17 hydrocarbon | $C_{17}H_{36}$, mp = 21° C. | Sigma-Aldrich Corp., Saint Louis, MO, US |
| C-18 hydrocarbon | $C_{18}H_{38}$, mp = 28-30° C. | Sigma-Aldrich Corp., Saint Louis, MO, US |
| C-19 hydrocarbon | $C_{19}H_{40}$, mp = 32-34° C. | Sigma-Aldrich Corp., Saint Louis, MO, US |
| C-20 hydrocarbon | $C_{20}H_{42}$, mp = 36.7° C. | Sigma-Aldrich Corp., Saint Louis, MO, US |
| C-21 hydrocarbon | $C_{21}H_{44}$, mp = 40.5° C. | Sigma-Aldrich Corp., Saint Louis, MO, US |
| C-22 hydrocarbon | $C_{22}H_{46}$, mp = 42° C. | Sigma-Aldrich Corp., Saint Louis, MO, US |
| C-23 hydrocarbon | $C_{23}H_{48}$, mp = 48-50° C. | Sigma-Aldrich Corp., Saint Louis, MO, US |

Test Methods

Largest Soluble Hydrocarbon (LSH): The LSH of each hydrofluoroolefin compound was determined by mixing the compound with hydrocarbons of varying molecular weight ($C_nH_{2n+2}$, where n=9 to 24) in a hydrofluoroolefin:hydrocarbon ratio of about 1:1 to 1:2 by weight at room temperature (25° C.) and at 50° C. The LSH value is reported as the value of n in the formula $C_nH_{2n+2}$ for the longest hydrocarbon which was compatible with the hydrofluoroolefin without exhibiting haze to the naked eye. A larger value of n is interpreted herein to indicate a greater ability of the hydrofluoroolefin to clean hydrocarbons.

Atmospheric lifetime: The atmospheric lifetime of Example 1 was determined from the rate of reaction with hydroxyl radicals. The pseudo-first order rate for the reaction of the gaseous hydrobromofluoroolefin with hydroxyl radical was measured in a series of experiments relative to reference compounds such as chloromethane and ethane. The measurements were performed in a 5.7 L, heated FTIR gas cell equipped with a polished semiconductor-grade quartz window. An Oriel Instruments UV Lamp, Model 66921 equipped with a 480 W mercury-xenon bulb was used to generate hydroxyl radicals by photolyzing ozone in the presence of water vapor. The concentrations of the hydrobromofluoroolefin and the reference compound were measured as a function of reaction time using an I-Series FTIR from Midac Corporation, Westfield, Mass., US. The atmospheric lifetime was calculated from the reaction rates for the hydrobromofluoroolefin relative to the reference compounds and the reported lifetime of the reference compounds as shown below:

$$\tau_x = \tau_r \cdot \frac{k_r}{k_x}$$

where $\tau_x$ is the atmospheric lifetime of hydrobromofluoroolefin, $\tau_r$ is the atmospheric lifetime of the reference compound, and $k_x$ and $k_r$ are the rate constants for the reaction of hydroxyl radical with hydrobromofluoroolefin and the reference compound, respectively.

Sample Preparation

Example 1: 2-Chloro-1,1,1,4,4,4-hexafluoro-3-methoxybut-2-ene via substitution of 2,3-dichloro-1,1,1,4,4,4-hexafluorobut-2-ene by MeOH in the presence of KOH

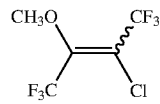

Potassium hydroxide (KOH, 24.1 g, 429 mmol) was added to methanol (70 mL) slowly to afford a basic solution which was added dropwise via a syringe to a three-neck round-bottom flask (equipped with a magnetic stir bar, temperature probe, and a water-cooled reflux condenser) containing 2,3-dichloro-1,1,1,4,4,4-hexafluorobutene (100 g, 429 mmol) and methanol (80 mL). The rate of addition of the basic methanol solution was such that the internal reaction mixture never exceeded 33° C. to avoid unwanted bis- and tris-ether formation. After complete addition, the resultant reaction mixture was allowed to stir for 16 hr without heating. To the mixture was then added $H_2O$ (50 mL) with stirring. The bottom fluorous layer was collected and analyzed by GC-FID analysis revealing a mixture containing 75% of the desired 2-chloro-1,1,1,4,4,4-hexafluoro-3-methoxybut-2-ene product. Concentric tube distillation (87° C., 760 mmHg) afforded purified 2-chloro-1,1,1,4,4,4-hexafluoro-3-methoxybut-2-ene (92.9 g, 66% yield). The purified composition was confirmed by GC-MS and $^{19}F$ NMR analysis.

Example 2. 2-Chloro-1,1,1,4,4,4-hexafluoro-3-(2,2,2-trifluoroethoxy)but-2-ene via substitution of 2,3-dichloro-1,1,1,4,4,4-hexafluorobut-2-ene by CF3CH2OH in the presence of $K_2CO_3$ in $CH_3CN$

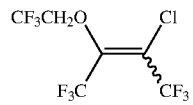

A 3-neck flask equipped with a magnetic stir bar, temperature probe, and water-cooled condenser was charged with 2,3-Dichloro-1,1,1,4,4,4-hexafluorobut-2-ene (11 g, 47 mmol), acetonitrile (11 mL), and potassium carbonate (7.2 g, 52 mmol). To the resultant stirring mixture was slowly added 2,2,2-trifluoroethanol (4.7 g, 47 mmol) dropwise over the course of 0.5 hr to prevent the reaction mixture from exceeding 30° C. After complete addition, the resultant mixture was allowed to stir overnight without heating. The reaction mixture was then charged with water (100 mL). The bottom fluorous layer was then separated from the aqueous phase. The bottom fluorous layer was collected and analyzed by GC-FID revealing a mixture containing 25% of the desired 2-chloro-1,1,1,4,4,4-hexafluoro-3-(2,2,2-trifluoroethoxy)but-2-ene product to provide an uncorrected GC yield of 25%.

Example 3 (E3). 2-Chloro-1,1,1,4,4,4-hexafluoro-3-((1,1,1,3,3,3-hexafluoropropan-2-yl)oxy)but-2-ene via substitution of 2,3-dichloro-1,1,1,4,4,4-hexafluorobut-2-ene by (CF3)2CHOH in the presence of K2CO3 in CH3CN

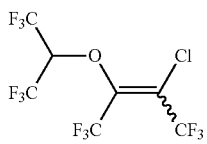

A 3-neck flask equipped with a magnetic stir bar, temperature probe, and water-cooled condenser was charged with 2,3-dichloro-1,1,1,4,4,4-hexafluorobut-2-ene (40 g, 171 mmol), acetonitrile (40 mL), and potassium carbonate (23.7 g, 172 mmol). To the resultant stirring mixture was slowly added 1,1,1,3,3,3-hexafluoropropan-2-ol (28.8 g, 155 mmol) dropwise over the course of 0.5 hr to prevent the reaction mixture from exceeding 30° C. After complete addition, the resultant mixture was heated to a mantle temperature of 60° C. followed by an overnight stir. The reaction mixture was then allowed to cool to room temperature followed by the addition of H$_2$O (250 mL). The bottom fluorous layer was then separated from the aqueous phase and was then subjected to concentric tube distillation (111° C., 760 mmHg) to afford 2-chloro-1,1,1,4,4,4-hexafluoro-3-((1,1,1,3,3,3-hexafluoropropan-2-yl)oxy)but-2-ene (59.6 g, 91% yield). Title compound was confirmed by GC-MS analysis.

Example 4: 1-Chloro-3,3,4,4,5,5-hexafluoro-2-methoxycyclopent-1-ene

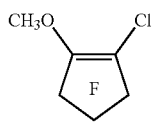

1-Chloro-3,3,4,4,5,5-hexafluoro-2-methoxycyclopentene was purchased from Sigma-Aldrich Corp. Saint Louis, Mo., US and used as received.

Example 5: 2-Chloro-1,1,1,4,4,4-hexafluoro-3-(2,2,2-trifluoroethoxy)but-2-ene via substitution of 1,2-dichloro-3,3,4,4,5,5-hexafluorocyclopent-1-ene by CF3CH2OH in the presence of KOH

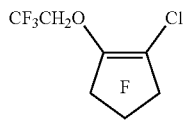

Potassium hydroxide (11.5 g, 204 mmol) was added to methanol (30.8 mL) slowly to afford a basic solution which was added dropwise via a syringe to a three-neck round-bottom flask (equipped with a magnetic stir bar, temperature probe, and a water-cooled reflux condenser) containing perfluoro-1,2-dichlorocyclopentene (50 g, 204 mmol) and methanol (20 mL). The rate of addition of the basic methanol solution was such that the internal reaction mixture never exceeded 33° C. to avoid unwanted bis- and tris-ether formation. After complete addition, the resultant reaction mixture was allowed to stir for 16 hr without heating. To the mixture was then added H$_2$O (50 mL) with stirring. The bottom fluorous layer was collected and analyzed by GC-FID revealing a mixture containing 68% of the desired 2-chloro-1,1,1,4,4,4-hexafluoro-3-(2,2,2-trifluoroethoxy) but-2-ene product to provide an uncorrected GC yield of 70%.

Results

Table 2 summarizes results of Largest Soluble Hydrocarbon (LSH) testing of Examples 1 and 4. Since the largest hydrocarbon used was C-23 (C$_{23}$H$_{48}$), an LSH of ">23" indicates that the hydrofluoroolefin was miscible with C$_{23}$H$_{48}$ without exhibiting haze. The results presented in Table 2 indicate that the hydrofluoroolefins of the present invention are highly suitable fluids for cleaning applications.

TABLE 2

| Largest Soluble Hydrogen | | |
|---|---|---|
| | LSH (n in C$_n$H$_{2n+2}$) | |
| Example | 25° C. | 50° C. |
| 1 | 19 | >23 |
| 4 | 19 | >23 |

The atmospheric lifetime of Example 1 was determined from its rate of reaction with hydroxyl radicals as described above and was determined to be 0.04 years.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows. All references cited in this disclosure are herein incorporated by reference in their entirety.

What is claimed is:

1. A composition comprising:
a compound having structural formula (I):

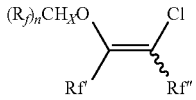

where $R_f$ is a linear or branched perfluoroalkyl group having 1-3 atoms; n is 0-2; x is 1-3; and $R_f'$ and $R_f''$ are (i) independently, a linear or branched perfluoroalkyl group having 1-8 carbon atoms; or (ii) are bonded together to form a ring structure having 4-8 carbon atoms;

with the provisos that:
when n is 0, then x is 3;
when n is 1 then x is 2; and
when n is 2 then x is 1; and
a hydrocarbon contaminant.

2. The composition of claim 1, wherein the hydrocarbon contaminant comprises a hydrocarbon having the formula $C_nH_{2n+2}$, where n is greater than 5.

3. The composition of claim 2, wherein the compound having structural formula (I) is present in the composition at an amount of at least 25% by weight based on the total weight of the composition.

4. The composition of claim 2, wherein the compound having structural formula (I) is present in the composition at an amount of at least 50% by weight based on the total weight of the composition.

5. The composition of claim 2, wherein the hydrocarbon contaminant is present in the composition at an amount of between 0.0001% and 20% by weight, based on the total weight of the compounds of structural formula (I) in the post-clean composition.

6. The composition of claim 1, wherein the composition further comprises a co-solvent.

7. The composition of claim 6, wherein said co-solvent comprises alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof.

8. The composition of claim 1, wherein the composition further comprises a surfactant.

9. The composition of claim 8, wherein the composition comprises from 0.1 to 5 percent by weight of the surfactant, based on the total weights of the compound having structural formula (I) and the surfactant.

10. The composition of claim 8, wherein the surfactant comprises a nonionic surfactant comprising an ethoxylated alcohol, an ethoxylated alkylphenol, an ethoxylated fatty acid, an alkylaryl sulfonate, a glycerolester, an ethoxylated fluoroalcohol, a fluorinated sulfonamide, or mixtures thereof.

11. A process for removing contaminants from a substrate, the process comprising the steps of:
contacting a substrate with a compound having structural formula (I):

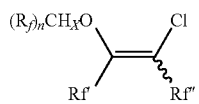

where $R_f$ is a linear or branched perfluoroalkyl group having 1-3 atoms; n is 0-2; x is 1-3; and $R_f'$ and $R_f''$ are (i) independently, a linear or branched perfluoroalkyl group having 1-8 carbon atoms; or (ii) are bonded together to form a ring structure having 4-8 carbon atoms;

with the provisos that
when n is 0, then x is 3;
when n is 1 then x is 2; and
when n is 2 then x is 1; and
wherein the contaminant comprises a hydrocarbon.

12. The process of claim 11, wherein the hydrocarbon contaminant comprises a hydrocarbon having the formula $C_nH_{2n+2}$, where n is greater than 5.

* * * * *